US012521121B2

(12) United States Patent
Demillo

(10) Patent No.: US 12,521,121 B2
(45) Date of Patent: Jan. 13, 2026

(54) RIGGERS BELT WITH INTEGRATED MEDICAL TOURNIQUET

(71) Applicant: The Government of the United States, as represented by the Secretary of the Air Force, Wright-Patterson AFB, OH (US)

(72) Inventor: Isaiah Demillo, Wichita Falls, TX (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 191 days.

(21) Appl. No.: 18/428,049

(22) Filed: Jan. 31, 2024

(65) Prior Publication Data

US 2025/0241655 A1 Jul. 31, 2025

(51) Int. Cl.
*A61B 17/132* (2006.01)
*A41F 9/00* (2006.01)

(52) U.S. Cl.
CPC .......... *A61B 17/1322* (2013.01); *A41F 9/002* (2013.01)

(58) Field of Classification Search
CPC ........................................................ A41F 9/002
See application file for complete search history.

(56) References Cited

U.S. PATENT DOCUMENTS

| | | | |
|---|---|---|---|
| 10,321,917 | B2 | 6/2019 | Steinbaugh et al. |
| 10,335,160 | B1 | 7/2019 | Holloman et al. |
| 10,765,437 | B1 | 9/2020 | Antonio |
| 11,298,139 | B2 | 4/2022 | Voros |
| 11,766,265 | B1 | 9/2023 | Antonio |
| 2021/0258332 | A1 | 8/2021 | Nance, II |
| 2021/0258395 | A1 | 8/2021 | Larson et al. |

OTHER PUBLICATIONS

Print out of website www.revmdx.com/parabelt Jan. 31, 2024.

*Primary Examiner* — Ryan J. Severson
(74) *Attorney, Agent, or Firm* — AFMCLO/JAZ; Richard M. Mescher

(57) ABSTRACT

A waist belt includes an elongate web having a first end and a second free end and a buckle coupled to the first end and configured to selectively secure the second free end. A rigid backing plate is secured at an inner side of the elongate web. A compression assembly includes an elongate compression strap secured at an inner surface of the elongate web at first and second spaced apart attachment points, and a windlass operably secured to the elongate compression strap between the first and second attachment points and outward of the rigid backing plate for selectively tightening the compression strap. The rigid backing plate and the elongate web each have at least one opening therein for passage of the elongate compression strap therethrough to the windlass. A retainer is integral with the rigid backing plate for securing the windlass against rotation when the elongate compression strap is tensioned.

20 Claims, 4 Drawing Sheets

RIGGERS BELT WITH INTEGRATED MEDICAL TOURNIQUET

RIGHTS OF THE GOVERNMENT

The invention described herein may be manufactured and used by or for the Government of the United States for all governmental purposes without the payment of any royalty.

FIELD OF THE INVENTION

The present invention relates generally to functional apparel and, more particularly, to a waist belt that can be used as a tourniquet during medical emergencies.

BACKGROUND OF THE INVENTION

The United States military did not use tourniquets in the past due to concerns about potential complications, such as tissue damage and limb loss. However, advancements in medical research and combat situations have led to a shift in this practice, and tourniquets are now utilized for controlling severe bleeding in military settings. While there are potential risks, such as tissue damage, the benefits of using tourniquets to save lives outweigh the risks. The military began to embrace the use of tourniquets more widely following the conflicts in Iraq and Afghanistan as advancements in medical research and technology led to the development of more efficient and safer tourniquet designs. Military personnel receive comprehensive training on the proper application of tourniquets to ensure they can effectively utilize them in combat situations.

Tourniquets are used primarily to achieve occlusion of arterial blood flow. A typical tourniquet includes a band tightly applied around a body part (an arm or a leg) in an attempt to stop severe bleeding or uncontrolled hemorrhage in an emergency situation. An example of prior tourniquets is a piece of rubber tubing that is wrapped around the limb and tied tightly. A stick is wound underneath the tubing and twisted until the tubing is tightened so that the bleeding is stopped. Once adequate pressure is applied on the limb, the stick is secured into its position to maintain the pressure.

Medical tourniquets are included in military first aid kits to ensure that personnel have access to them in emergency situations. However, military personnel are required to carry an increasing amount of equipment, and they can at times be separated from their first aid kits during combat. As a result, it has been suggested to integrate a medical tourniquet with an article of apparel such as a waist belt which is always at hand when worn. For example, U.S. Pat. No. 10,321,917 to Steinbaugh et al. and entitled "Tourniquet Belt" and U.S. Pat. No. 10,335,160 to Holloman et al. and entitled "Tourniquet Belt." However, in military applications such waist belts must both meet uniform regulations and be of a more efficient and safer tourniquet design that now allows it to be used by military personnel. Additionally, when the belts are riggers belts, they have relatively high strength requirements.

Accordingly, there is a need for an article of functional clothing that incorporates a medical tourniquet that both meets uniform and strength requirements and is of an efficient and safe tourniquet design that allows it to be used by military personnel.

SUMMARY OF THE INVENTION

The present invention overcomes the foregoing problems and other shortcomings, drawbacks, and challenges of meeting uniform requirement, strength requirements, and/or safe tourniquet requirements. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, a waist belt comprises an elongate web having a first end and a second free end, a buckle coupled to the first end of the elongate web and configured to selectively secure the second free end of the elongate web, a rigid backing plate secured at an inner side of the elongate web, and a compression assembly. The compression assembly comprises an elongate compression strap secured at an inner surface of the elongate web at first and second spaced apart attachment points, and a windlass operably secured to the elongate compression strap between the first and second attachment points and outward of the rigid backing plate for selectively tightening the compression strap. The rigid backing plate has at least one opening therein for passage of the elongate compression strap therethrough to the windlass.

According to another embodiment of the present invention, a waist belt comprises an elongate web having a first end and a second free end, a buckle coupled to the first end of the elongate web and configured to selectively secure the second free end of the elongate web, and a compression assembly comprising an elongate compression strap secured at an inner surface of the elongate web at first and second spaced apart attachment points, and a windlass located outward of the elongate web and operably secured to the elongate compression strap between the first and second attachment points for selectively tightening the compression strap. The elongate web has at least one opening therein for passage of the elongate compression strap therethrough to the windlass.

According to yet another embodiment of the present invention, a waist belt comprises an elongate web having a first end and a second free end, a buckle coupled to the first end of the elongate web and configured to selectively secure the second free end of the elongate web, and a compression assembly. The compression assembly comprises an elongate compression strap secured at an inner surface of the elongate web at first and second spaced apart attachment points, and a windlass outward of the elongate web and operably secured to the elongate compression strap between the first and second attachment points for selectively tightening the compression strap. At least one first fastener is secured on an outer surface of the elongate web between the windlass and the second free end and at least one second fastener secured on the outer surface of the elongate web between the windlass and the first fastener so that the second free end can be looped back over the elongate web to secure the first fastener to the second fastener. The first fastener is one of a hook fastener and a loop fastener and the second fastener is the other of a hook fastener and a loop fastener.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Figure 1:
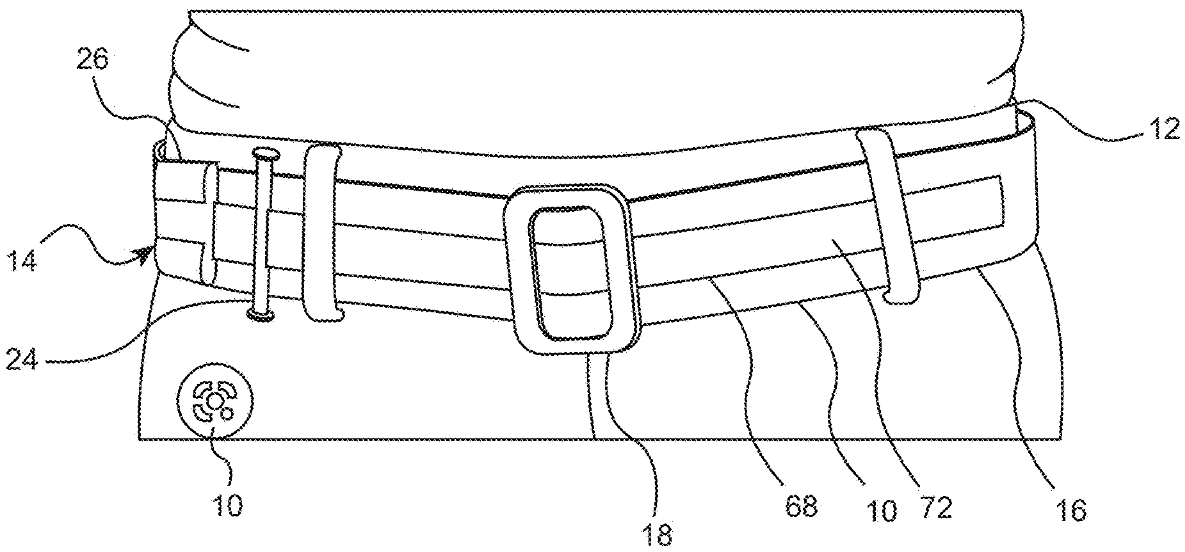
FIG. 1 is a front view of a person's waist wearing a belt according to the present invention.

FIG. 1 illustrates a belt 10 extending about a waist 12 of a user having an integrated medical tourniquet 14 according to an embodiment of the present invention. The illustrated belt 10 is a riggers belt, but it is noted that any other suitable type of belt can alternatively be utilized. A riggers belt is a heavy-duty belt used to carry equipment and gear and can provide a point of attachment for rappelling and/or rescue operations. Riggers belts are frequently used by military, law enforcement, rescue, and civilian personnel. Riggers belts are constructed to hold significant loads of equipment such as pistols and holsters, knives and batons, handcuffs, sheaths, and rescue tools etc. Riggers belts are typically constructed to have at least 5,000 lbs. of tensile strength and sometimes at least 7,000 lbs. of tensile strength.

The illustrated riggers belt 10 includes a high-strength nylon web 16. However, the web 16 can comprise any other suitable material such as, for example but not limited to, polyester webbing, or the like. The web 16 preferably has a width of about 1.5 inches to 2 inches, and more preferably a width of about 1.75 inches. The illustrated web 16 preferably has a length for extending once around the waist 12 of the user with a small overlap so that it can provide a snug fit. It is noted that the length of the web 16 will vary depending on the size of the user's waist 12 and/or the type of buckle 18 utilized. It is noted that the web 16 can alternatively have any other suitable configuration.

The illustrated belt 10 also includes a buckle 18 for securing the web 16 about the waist 12 of the user. The illustrated buckle 18 is a parachute-type buckle. However, it is noted that any other suitable type of buckle 18 can alternatively be utilized such as, for example but not limited to, pass through buckles, tongue buckles, quick connect buckles, and the like. Each of these types of buckles 18 can be adjusted to form a snug fit about the user's waist 12.

The illustrated parachute buckle 18 has a generally rectangular-shaped frame 20 and a vertically-extending knurled bar 22 (best shown in FIG. 3) within the frame 20 to form inner and outer slots within the frame 20 on opposed side of the knurled bar 22. The parachute buckle 18 can be formed of steel, aluminum, plastic, composite, or any other suitable material. The illustrated frame has a height of about 1⅞ inches to cooperate with the width of 1.75 inches for the illustrated frame. However, the frame can alternatively any other suitable size. One end of the web 16 is permanently or otherwise secured to the frame 20. For example, but not limited to, the web 16 can be looped around a portion of the frame 20 and secured in place by stitching. It is noted that the buckle 18 can alternatively have any other suitable configuration and/or can be of any other suitable type.

The illustrated parachute buckle 18 is secured about the user's waist 12 by capturing the free end of web 16 between the knurled bar 22 and the buckle frame 20. In some parachute buckles, a spring-loaded slider bar is provided to maintain constant tension on the knurled bar. The free end of the web 16 is woven into the buckle 18 by passing the web 16 under the frame 20 and up through the inner slot, over the knurled bar 22, then back down through the outer slot and under the outer portion of the frame 20 so that the web 16 is folded back on top of itself. Typically, about three inches of the free end of the web 16 extends out of the buckle 18. It is noted that the parachute buckle 18 can alternatively operate in any other suitable manner.

The illustrated medical tourniquet 14 is integrated into the belt 10 and is configured for emergency trauma conditions. When the belt is removed from the user's waist 12, the medical tourniquet 14 functions to be easily applied to a limb of a wounded/injured person to terminate excessive bleeding and to maintain sufficient pressure until medical treatment can be performed. It is noted that when the belt 10 according to the present invention is worn, the sole visual indicator that the medical tourniquet 14 is present within the belt 10 is that only a windlass 24 (in a vertical position) and a windlass retainer 26 are visible. Thus, the illustrated belt 10 meets current uniform regulations. It is also noted that the belt 10 according to the present invention has a core construction of the continuous high-strength web 16 is secured to buckle 18 and extends entirely around the waist of the user's waist 12. Thus, the illustrated belt 10 meets the strength requirements of a riggers belt.

Figure 2B:
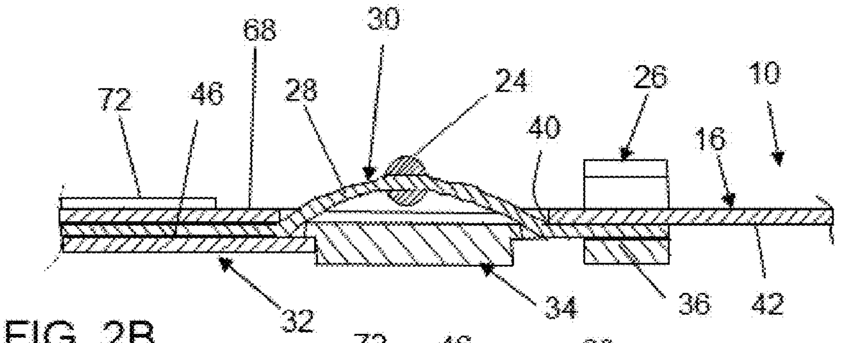
FIG. 2B is a cross sectional view taken along line 2B-2B of FIG. 2A.
Figure 2C:
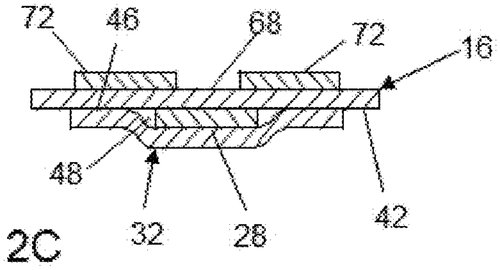
FIG. 2C is a cross sectional view taken along line 2C-2C of FIG. 2A.
Figure 2A:
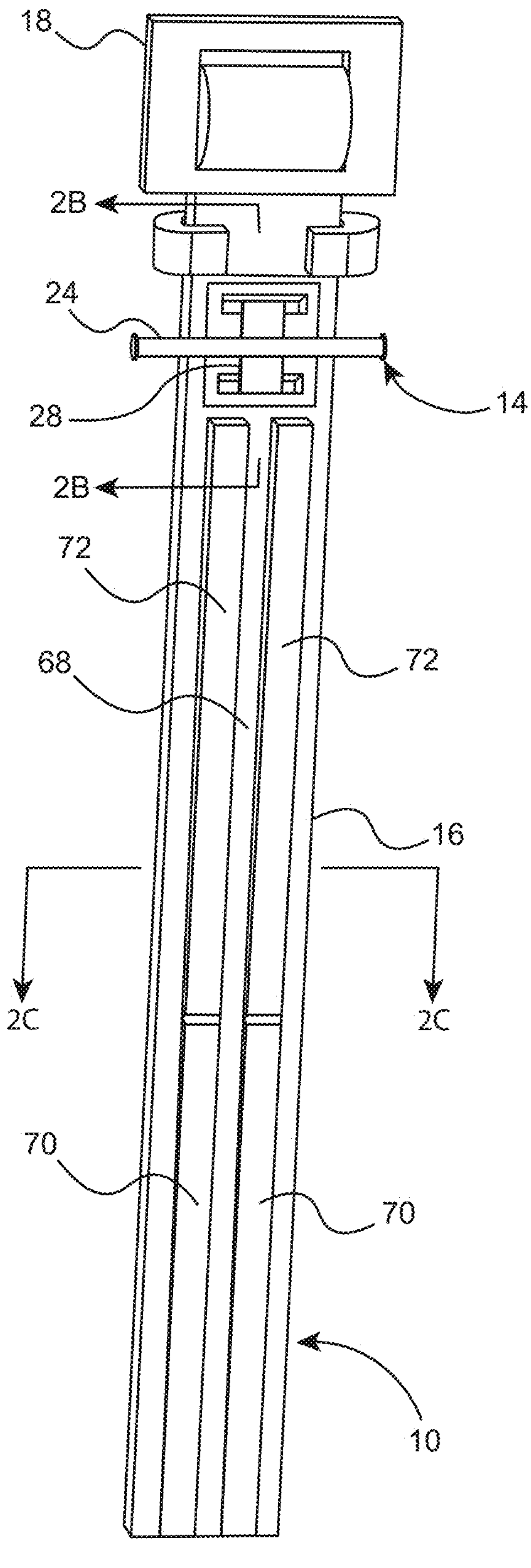
FIG. 2A is an outer view of a belt according to the present invention.
Figure 3:
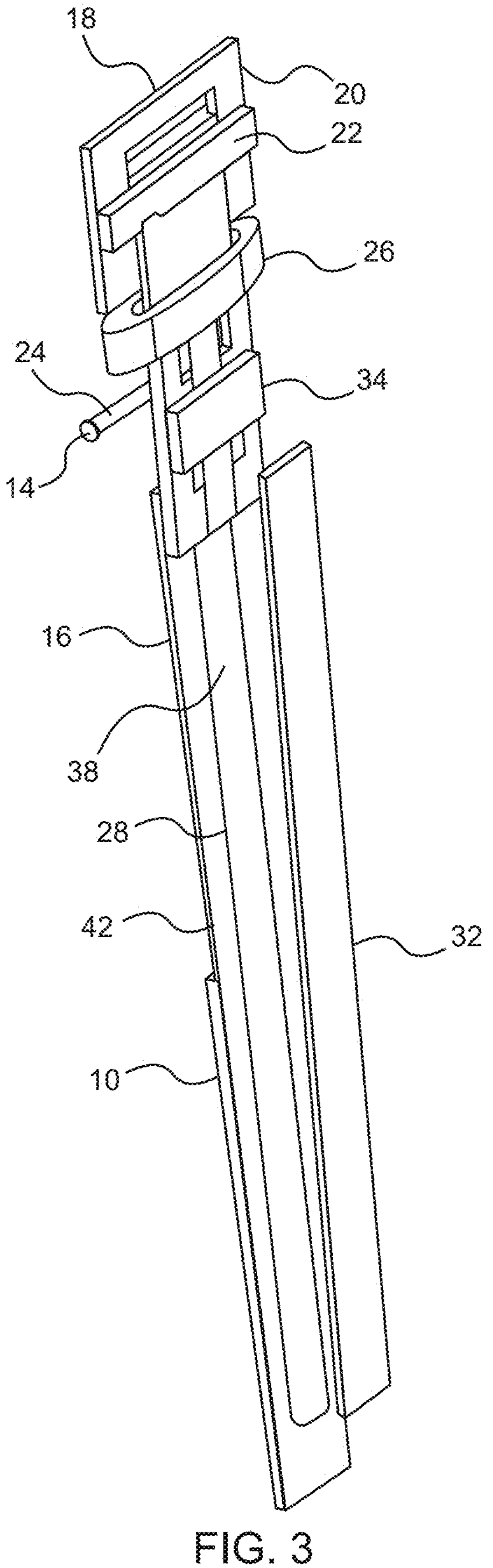
FIG. 3 is a perspective and partially exploded view of an inner side the belt of FIGS. 2A and 2B.

FIGS. 2A, 2B, and 3, illustrate another belt 10 having an integrated medical tourniquet 14 according to an embodiment of the present invention. The illustrated belt 10 is a riggers belt as described hereinabove. The illustrated medical tourniquet 14 includes a compression assembly 30, an overlay strip 32, a backing plate 34, and a windlass retainer 26. The compression assembly 30 comprises an elongate compression strap 28 and a windlass 30 to provide the compressive force applied by the tourniquet.

The illustrated elongate compression strap 28 has a length that is nearly as long as the web 16. The elongate compression strap 28 is preferably sized to extend from the buckle side of the backing plate 34 located near the buckle 18 to a location near the free end of the web 16 but short of the portion of the web 16 that extends past the buckle 18. It is noted that the elongate compression strap 28 can alternatively have any other suitable length but should not have a length longer than the web 16. The illustrated elongate compression strap 28 has a width that is about 0.5 inches but can be any other suitable width that is less than the width of the overlay strip described herein below. Ends of the elongate compression strap 28 are double stitched to the web 16 at anchor positions 36, 38. It is noted that the ends of the elongate compression strap 28 can alternatively be attached to the web 16 in any other suitable manner. Between the anchor positions 36, 38, the elongate compression strap 28 is unattached to the web 16. The illustrated compression strap 28 has a single layer of woven nylon material. However, the elongate compression strap can alternatively comprise any other suitable material or materials. For example, but not limited to, the elongate compression strap 28 can have two layers with a first or upper layer of woven nylon material and a second or lower) layer of smooth nylon material stitched together along their longitudinal length. The layer of smooth nylon material can reduce friction between the elongate compression strap 28 and the web 16 when the elongate compression strap 28 slides along the web 16 as described in more detail hereinafter. Alternatively, the layer of smooth nylon material can be secure to the web 16 rather than the elongate compression strap 28. In any case the elongate compression strap 28 is configured to withstand substantial longitudinal stresses. It is noted that the elongate compression strap 28 can alternatively have any other suitable configuration.

The elongate compression strap 28 extends from the first anchor position 36 along the inner side of the web 16 at the backing late 34, extends outward through a window or opening 40 in the web 16 and loops back inward through the opening 40, and continues to extend along the inner side of the web 16 past the backing plate 34 until it reaches the second anchor position 38. The elongate compression strap 28 is generally disposed to slide across the inner surface 42 of the web 15.

Figure 4A:
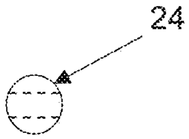
FIG. 4A is a top view of a windlass of the belt of FIGS. 2A, 2B, and 3.
Figure 4B:
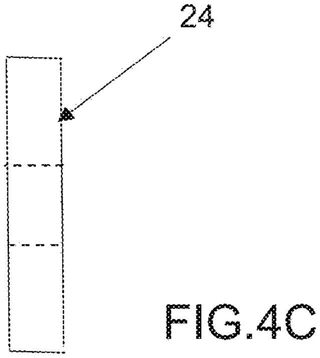
FIG. 4B is an outer elevational view of the windlass of FIG. 4A.
Figure 4C:
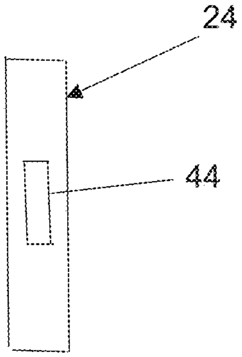
FIG. 4C is an outer elevational view of the windlass of FIGS. 4A and 4B.
Figure 5A:
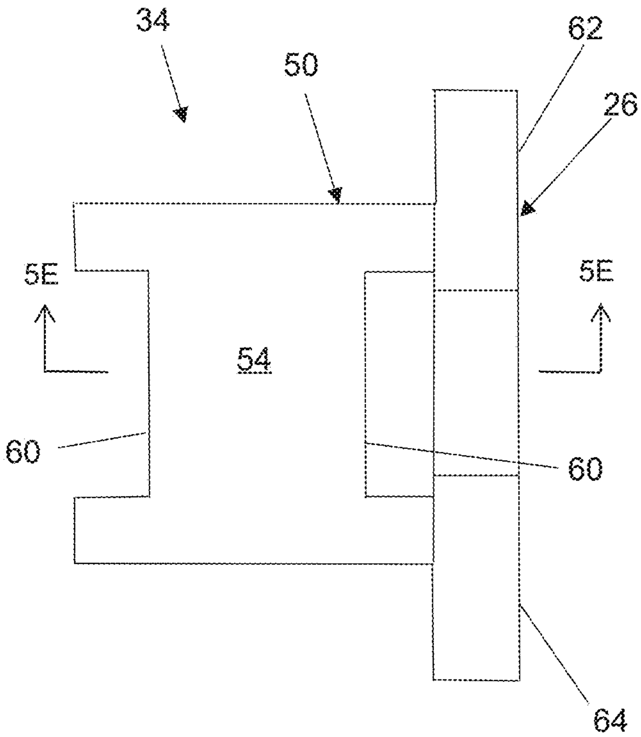
FIG. 5A is an outer elevational view of a back plate of the belt of FIGS. 2A, 2B, and 3.
Figure 5B:
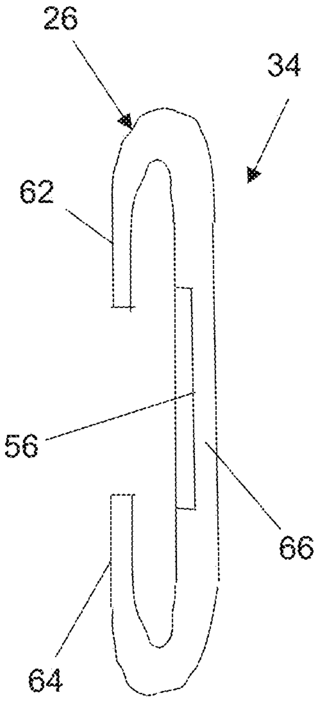
FIG. 5B is a front side elevational view of the back plate of FIG. 5A.
Figure 5C:
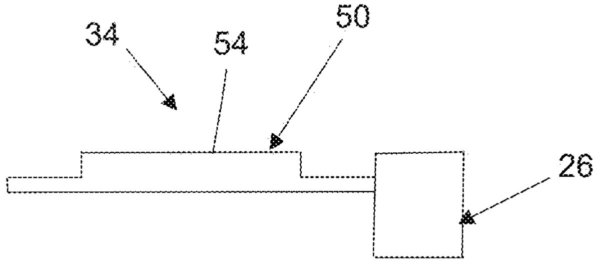
FIG. 5C is atop plan view of the back plate of FIGS. 5A and 5B.
Figure 5D:
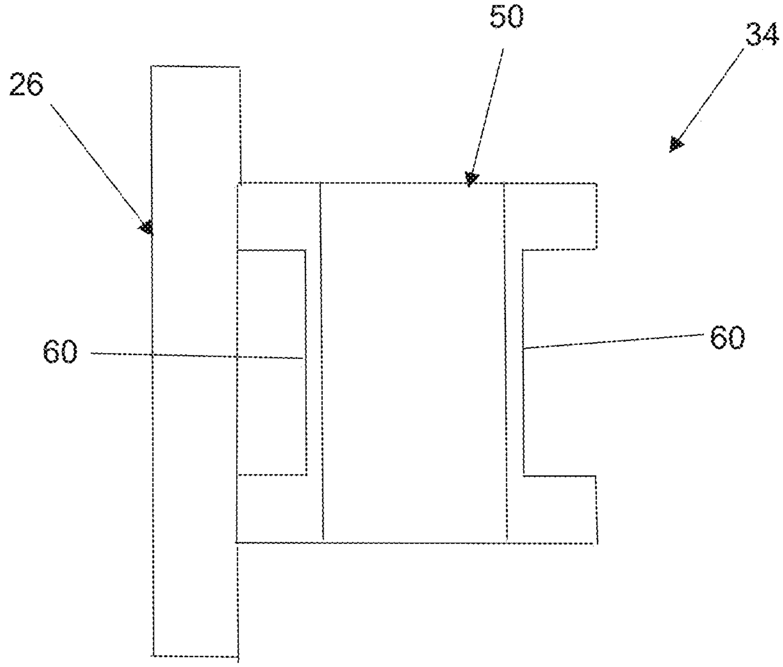
FIG. 5D is an inner elevational view of the back plate of FIGS. 5A to 5C.
Figure 5E:
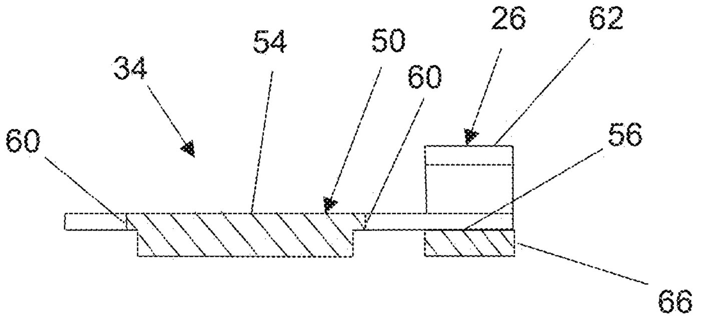
FIG. 5E is a cross sectional view taken along line 5E-5E of FIG. 5A.

As best shown in FIGS. 4A to 4C, the windlass 24 is a sturdy, elongated rod-like member which has a length greater than the width of the web 16. The illustrated windlass 24 has a length of about 3.25 inches for use with the illustrated web 16 having a width of about 1.75 inches. Medially along the length of the windless 24 is a lengthwise extending slot 44 extending entirely therethrough. The slot 44 is sized to receive the elongate compression strap 28 therethrough. The illustrated windlass 24 is positioned along the loop in the elongate compression strap 28 located above the backing plate 34. Configured in this manner, rotating the windlass 20 winds the elongate compression strap 28 to tension the elongate compression strap 28. The windlass 26 may have various configurations which facilitate manual gripping such as, for example but not limited to, knurling, ridges, and the like. The windlass 26 can be formed of heavy-duty plastic, steel, aluminum, composites, or the like. It is noted that the windlass 24 can alternatively have any other suitable configuration.

The overlay strip 32 of woven nylon material which has a length slightly longer than the elongate compression strap 28 and a width greater than the width of the compression strap and no greater than the width of the web 16. It is noted that the overlay strip 32 can alternatively comprise any other suitable material. The illustrated overlay strip 32 has a width of approximately 2 inches. It is noted that the overlay strip 32 can alternatively any other suitable width. The overlay strip 32 is stitched to the web 14 at opposing longitudinal sides to the web 14. It is noted that the overlay strip 32 can alternatively be secured to the web 14 in any other suitable manner. The inner surface 46 of the overlay strip 32 and the inner surface 42 of web 16 form a passage or slide therebetween (best shown in FIG. 2C). The elongate compression strap 28 moves within the passage or slide 48 when tensioned by winding the windlass 24, as will be further described hereinbelow. It is noted that the overlay strip 32 can alternatively have any other suitable configuration.

As best shown in FIGS. 5A to 5E, the illustrated backing plate 34 is located along the web 16 near the buckle 18 and includes a main body 50 and a retainer 26 that are integrally formed as one component. However, it is noted that alternatively the main body 50 and the retainer 26 can alternatively be formed as separate components. The illustrated retainer 26 is positioned on the end of the backing plate 50 facing towards the buckle 18. However, the retainer 26 can alternately be positioned on the end of the backing plate 34 facing towards the free end of the web 16. The illustrated backing plate 34 is formed of a rigid plastic. However, it is noted that the backing plate 34 can alternatively be formed of any other suitable material such as, but not limited to, steel, aluminum, composite, and the like. The backing plate 34 can alternative have any other suitable configuration, The main body 50 includes a rectangular shaped and generally planar outward-facing surface 54 for engagement with a segment of the inner surface 42 of the web 16. The retainer 26 also has a rectangular shaped and generally planar outward-facing surface 56 for engagement with a segment of the inner surface 42 of the web 16 and is contiguous with the outward-facing surface 54 of the main body 50. The width of the illustrated outward-facing surfaces 54, 56 have a width generally equal to the width of the web 16. With the inner surface 42 of the web 16 in engagement with the outward-facing surfaces 54, 56, the web 16 horizontally passes across both the main body 50 and the retainer 26. The illustrated web 16 is secured to the backing plate 16 in this position. However, the web 16 can alternatively or additionally be secured to the backing plate 34 by for example, but not limited to, rivets, straps, and the like.

The web 16 has a rectangular shaped window or opening 40 formed therein that is sized smaller than the width of the web 16 so that the web 16 remains a single continuous web from the buckle 18 to the free end. The opening 40 is positioned over the outward facing surface 54 of the main body 50. Formed within the main body 50 are laterally extend notches 60 on each end of the main body 50. The notches each have a width smaller than then the web 16 and have a length that extends below a portion of the opening in the web so that the elongate compression strap 28 can pass through each of the notches 60 and the opening 40 to form the loop of the elongate compression strap 28 to which the windlass 24 is secured outward of the opening of the web 16 (best seen in FIG. 2B. The illustrated main body 50 has a central portion with increased thickness. The illustrated overlay strip 32 terminates at the end of the main body 50. It is noted that the main body 50 can alternatively have any other suitable configuration.

The illustrated retainer 26 is configured to form opposed C-shaped catches 62, 64 connected at lower ends by a crosspiece 66. The illustrated crosspiece 66 is integral with the main body 50. The catches 62, 64 are configured and dimensioned to receive and capture the windlass when the elongate compression strap 28 is tensioned as described hereinbelow. The illustrated catches 62, 64 have an interior separation of about 2 inches and have longitudinal edges which are separated by about 1 inch. The retainer 26 is preferably formed of a rigid plastic but can alternatively be formed of, for example but not limited to, steel, aluminum, composite, or the like. It is noted that the retainer 26 can alternatively have any other suitable configuration.

The outer surface 68 of the web 16 has hook-and-loop fasteners 70, 72 secured thereto. In the illustrated embodiment, a pair of parallel and laterally faced-apart strips of hook fasteners 70 extending from near the backing plate 34 to a location about midway between the backing plate 34 and the free end of the web 16, and a pair of parallel and laterally faced-apart strips of loop fasteners 72 extending from hook fasteners 70 to the free end of the web 16. It is noted that the hook-and-loop fasteners 70, 72 can alternatively have any other suitable configuration such as, for example but not limited to, there can be a single strip of hook fastener 70 and a single strip of loop fastener 72 (shown in FIG. 1) and/or the location of the strips of hook and loop fasteners 70, 72 can be reversed.

In operation, the belt 10 is removed from the wearer and is wrapped around a limb having a wound (not illustrated) between the heart and the wound of the injured person. The free end of the web 16 is inserted directly through buckle 18 and pulled tight around the limb with the overlay strip 32 engaging against the limb. The web 16 functions as a flexible highly conforming support structure for the tourniquet so that upon application, the tourniquet more effectively conforms to a shape about the limb that is optimal for constriction purposes. The excess web 16 is then folded back onto itself and secured by engaging the strips of loop fastener 70 with the strips of hook fastener 72 so that a secure tight fit of the web 16 about the limb is obtained. The hook and loop fastener connection 70, 72 provides a large connection interface and support for securing the tourniquet at a maximum initial tensioning without the risk of slippage. The hook and loop fastener connection 70, 72 also facilitates an easier and more effective one-handed application in cases where the tourniquet is being self-applied.

Additional pressure is applied by rotating the windlass 24 which causes the elongate compression strap 28 to tighten more about the limb. When sufficient pressure is obtained on the elongate compression strap 28 to terminate bleeding, one end of the windlass 24 is inserted into a catch 62, 64 so that the windlass 24 is captured by the retainer 26 against rotation in the unwinding direction to secure the windlass 24 with enhanced tourniquet pressure being maintained on the limb.

Rotation of the windlass 24 causes the elongate compression strap 28 to wrap about itself outside slide 48 and draws the elongate compression strap 28 out of the slide and through the backing plate 34 toward the windlass 24 thereby effectively tensioning the elongate compression strap 28 after it is wrapped around the limb. The backing plate 34 ensures that the elongate compression strap 28 retains it shape in full engagement with the limb and only deforms once outside the backing plate as the elongate compression strap 28 is wound by rotation of the windless 24.

With the windless 24 secured in the retainer 26, the occluding pressure on the wound is effectively and reliably maintained until appropriate medical assistance has been obtained.

The terms "comprises," "comprising," "includes," "including," "has," "having," or any other variations thereof used herein, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Reference to "one embodiment," "certain embodiments," "an embodiment," "implementation(s)," "aspect(s)," or similar terms used herein means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C." An exception to this definition will occur only when a combination of elements, functions, steps, or acts are in some way inherently mutually exclusive. Also, grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

All patents, patent applications (and any patents which issue thereon, as well as any corresponding published foreign patent applications), publications, and other documents mentioned throughout this description are hereby incorporated by reference herein. It is expressly not admitted, however, that any of the documents incorporated by reference herein teach or disclose the present invention.

The words "about," "approximately," or the like, when accompanying a numerical value, are to be construed as indicating a deviation as would be appreciated by one of ordinary skill in the art to operate satisfactorily for an intended purpose.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

For simplicity and clarity of illustration, reference numerals may be repeated among the figures to indicate corresponding or analogous elements. Numerous details are set forth to provide an understanding of the embodiments described herein. The embodiments may be practiced without these details. In other instances, well-known methods, procedures, and components have not been described in detail to avoid obscuring the embodiments described. The description is not to be considered as limited to the scope of the embodiments described herein.

References herein to items in the singular should be understood to include items in the plural, and vice versa, unless explicitly stated otherwise or clear from the text.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A waist belt comprising:

an elongate web having a first end and a second free end;

a buckle coupled to the first end of the elongate web and configured to selectively secure the second free end of the elongate web;

a rigid backing plate secured at an inner side of the elongate web; and a compression assembly comprising an elongate compression strap secured at an inner surface of the elongate web at first and second spaced apart attachment points, and a windlass operably secured to the elongate compression strap between the first and second attachment points and outward of the rigid backing plate for selectively tightening the compression strap;

wherein the rigid backing plate has at least one opening therein for passage of the elongate compression strap therethrough to the windlass.

2. The waist belt according to claim 1, wherein the elongate web has at least one opening therein for passage of the elongate compression strap therethrough to the windlass.

3. The waist belt according to claim 1, wherein the rigid backing plate has a pair of first and second spaced-apart openings therein for passage of the elongate compression strap therethrough to the windlass.

4. The waist belt according to claim 1, further comprising a retainer integral with the rigid backing plate for securing the windlass against rotation when the elongate compression strap is tensioned by the windlass.

5. The waist belt according to claim 1, wherein the rigid backing element is attached to the elongate web at a position closer to the first end than to the second free end of the elongate web.

6. The waist belt of claim 5, wherein at least one first fastener is secured on an outer surface of the elongate web between the rigid backing plate and the second free end and at least one second fastener secured on the outer surface of the elongate web between the rigid backing plate and the first fastener so that the second free end can be looped back over the elongate web to secure the first fastener to the second fastener, and wherein the first fastener is one of a hook fastener and a loop fastener and the second fastener is the other of a hook fastener and a loop fastener.

7. The waist belt of claim 1, wherein the waist belt is a riggers belt, and the elongate web has a tension strength of at least 5000 pounds.

8. The waist belt of claim 7, wherein the buckle is a parachute buckle.

9. A waist belt comprising:

an elongate web having a first end and a second free end;

a buckle coupled to the first end of the elongate web and configured to selectively secure the second free end of the elongate web; and a compression assembly comprising an elongate compression strap secured at an inner surface of the elongate web at first and second spaced apart attachment points, and a windlass located outward of the elongate web and operably secured to the elongate compression strap between the first and second attachment points for selectively tightening the compression strap;

wherein the elongate web has at least one opening therein for passage of the elongate compression strap therethrough to the windlass.

10. The waist belt according to claim 9, wherein the elongate web has an opening therein for passage of the elongate compression strap therethrough to the windlass.

11. The waist belt according to claim 9, wherein the windlass is located at a position closer to the first end than to the second free end of the elongate web.

12. The waist belt of claim 11, wherein at least one first fastener is secured on an outer surface of the elongate web between the rigid windlass and the second free end and at least one second fastener secured on the outer surface of the elongate web between the windlass and the first fastener so that the second free end can be looped back over the elongate web to secure the first fastener to the second fastener, and wherein the first fastener is one of a hook fastener and a loop fastener and the second fastener is the other of a hook fastener and a loop fastener.

13. The waist belt of claim 9, wherein the waist belt is a riggers belt, and the elongate web has a tension strength of at least 5000 pounds.

14. The waist belt of claim 13, wherein the buckle is a parachute buckle.

15. A waist belt comprising:

an elongate web having a first end and a second free end;

a buckle coupled to the first end of the elongate web and configured to selectively secure the second free end of the elongate web; and a compression assembly comprising an elongate compression strap secured at an inner surface of the elongate web at first and second spaced apart attachment points, and a windlass outward of the elongate web and operably secured to the elongate compression strap between the first and second attachment points for selectively tightening the compression strap;

wherein at least one first fastener is secured on an outer surface of the elongate web between the windlass and the second free end and at least one second fastener secured on the outer surface of the elongate web between the windlass and the first fastener so that the second free end can be looped back over the elongate web to secure the first fastener to the second fastener, and wherein the first fastener is one of a hook fastener and a loop fastener and the second fastener is the other of a hook fastener and a loop fastener.

16. The waist belt according to claim 15, wherein the elongate web has at least one opening therein for passage of the elongate compression strap therethrough to the windlass.

17. The waist belt according to claim 15, wherein the windless is located at a position closer to the first end than to the second free end of the elongate web.

18. The waist belt of claim 15, wherein the waist belt is a riggers belt, and the elongate web has a tension strength of at least 5000 pounds.

19. The waist belt of claim 18, wherein the buckle is a parachute buckle.

20. The waist belt of claim 15, further comprising a rigid backing plate secured at an inner side of the elongate web, and wherein the rigid backing plate has at least one opening therein for passage of the elongate compression strap therethrough to the windlass.

* * * * *